United States Patent [19]

Rizkalla

[11] Patent Number: 5,376,003
[45] Date of Patent: Dec. 27, 1994

[54] DEFLECTOR SHIELD FOR A DENTAL AIR/WATER/SPRAY SYRINGE

[76] Inventor: Adel J. Rizkalla, 7104 Penguin Pl., Falls Church, Va. 22040

[21] Appl. No.: 39,737

[22] Filed: Mar. 30, 1993

[51] Int. Cl.5 ............................................. A61C 1/16
[52] U.S. Cl. ..................................... 433/116; 433/80
[58] Field of Search ......................... 433/80, 116, 166

[56] References Cited

U.S. PATENT DOCUMENTS

| | | | |
|---|---|---|---|
| 3,858,368 | 1/1975 | Cocherell et al. | 433/166 |
| 4,424,036 | 1/1984 | Lokken | 433/116 |
| 4,611,992 | 9/1986 | Lokken | 433/116 |
| 4,850,868 | 7/1989 | Wright et al. | 433/116 |
| 5,067,899 | 11/1991 | Paschal | 433/116 |
| 5,197,876 | 3/1993 | Coston | 433/116 |

FOREIGN PATENT DOCUMENTS 14652  10/1933  Australia ........................... 433/80

*Primary Examiner*—John J. Wilson
*Attorney, Agent, or Firm*—Diller, Ramik & Wight

[57] ABSTRACT

A deflector shield is defined by a one-piece homogeneous body of polymeric/copolymeric synthetic transparent plastic material defined by a central portion having an opening and a peripheral portion generally surrounding the opening, the deflector shield is slipped upon a dental air/water/spray syringe and when thus positioned a concave surface is positioned immediately adjacent an end of the syringe and deflects the material impinging thereagainst and redirects the flow path of the impinging material away from the operator/dentist/assistant.

4 Claims, 1 Drawing Sheet

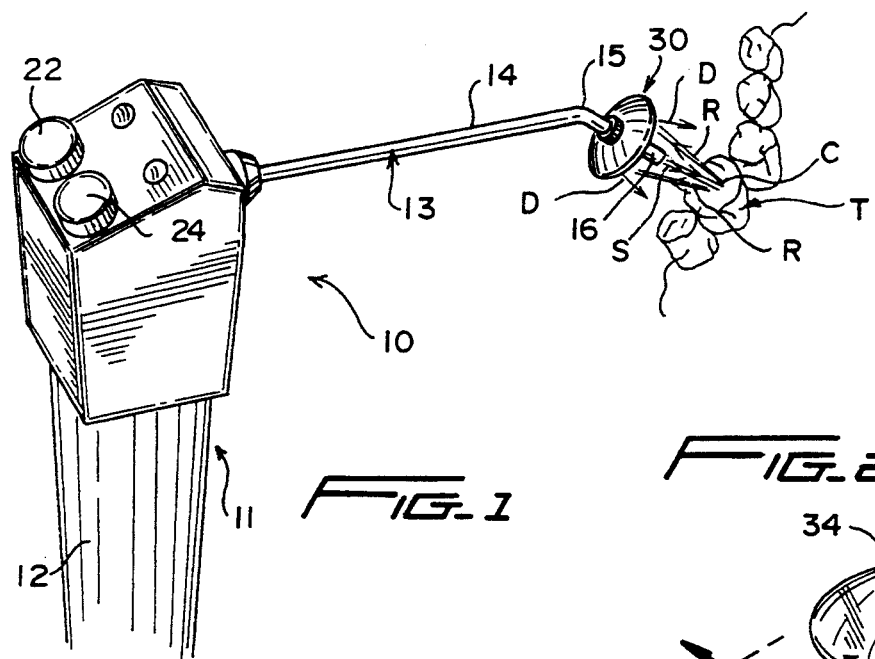
FIG_1
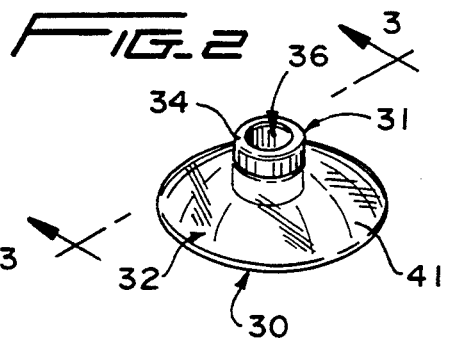
FIG_2
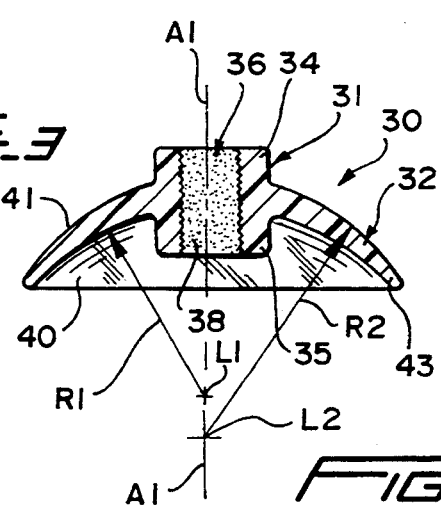
FIG_3
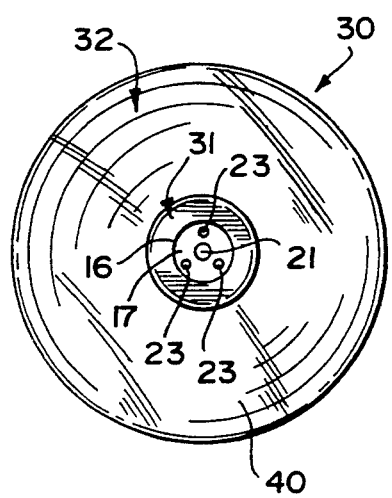
FIG_4
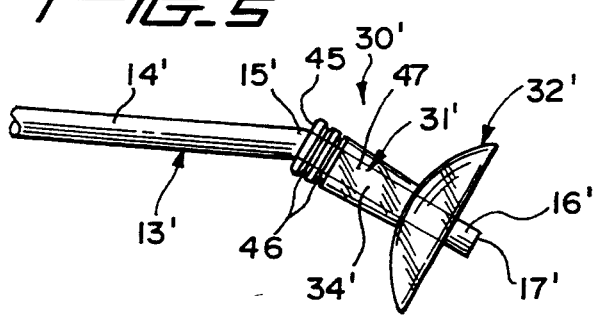
FIG_5
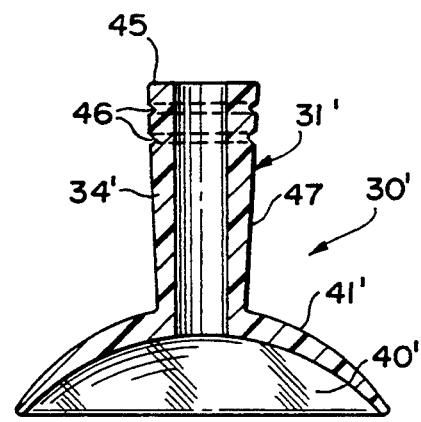
FIG_6

DEFLECTOR SHIELD FOR A DENTAL AIR/WATER/SPRAY SYRINGE

BACKGROUND OF THE INVENTION

An indispensable part of the dental operatory equipment is the dental air/water/spray syringe. A conventional air/water/spray syringe includes a hand piece or handle, a pair of buttons and a nozzle which normally includes a central port or orifice for emitting water, a plurality of peripheral orifices generally spaced 120° from each other for emitting air. The two buttons are selectively operable for controlling the emission of air alone, water alone, or both in the form of a spray or a mist. Such an air/water/spray syringe is used almost every time a dentist provides care for a patient, whether it is only by way of a dental examination or actual treatment. Frequently a dentist may direct air to dry an area moist with saliva or blood for better visibility, or may direct an air/water/spray or jet to clean debris. Also, the prevailing use of adhesive resins has become an essential part of practicing dentistry, and before applying such adhesive resins, the tooth surface is "conditioned" (etched) by applying an acid, such as phosphoric acid, for varying periods of time. Such acid must be flushed by directing a pin point copious water spray to the area for at least sixty (60) seconds. During this time the dentist has to keep his eye on the very spot to be rinsed to insure that proper rinsing has been achieved. During such pressurized application of air/water or an air/water spray into the mouth of a patient, the latter and any entrained admixed material can be reflected outwardly toward the dentist/operator/assistant. Such reflection outwardly from a patient's mouth is particularly common during cavity preparation due to the very nature of this operation. Prior to placing the filling material into the prepared tooth cavity, air and/or water is directed into the prepared cavity to cleanse and dry ,the same, and the cavity itself reflects the latter fluid and any materials admixed therewith back toward the operator's/dentist's/assistant's neck, eyes or the like. Such reflected admixed fluid might well be a mixture of saliva, blood, acid or similar debris. Needless to say, the latter creates a significant and serious risk, particularly in this day and age of presently incurable communicable diseases, such as AIDS (Acquired Immune Deficiency Syndrome) as the end effect of HIV (Humanimmuno Deficiency Virus).

U.S. Pat. No. 4,424,036 issued on Jan. 3, 1984 in the name of Oddvin Lokken discloses an anti-splash device for attachment to a dental tool which delivers water from the head thereof during use. The anti-splash device is an elongated, hollow member which includes an interior member for securing the hollow member to the head of the dental tool. The hollow member is thus in surrounding relationship to and spaced from the water delivery apparatus, and though it intends to provide anti-splash functions, the very construction thereof and particularly the space between the anti-splash device and the dental tool prevents optimum intended functioning thereof.

U.S. Pat. No. 4,611,992 issued on Sep. 16, 1986 to Oddvin Lokken discloses another anti-splash device which is also attached to a dental tool which delivers an aqueous fluid from a nozzle. The anti-splash device is an inverted U-shaped member having a base and integral opposed legs depending therefrom. One of the legs has a bore through which the nozzle of the dental tool projects and the base provides an area through which an associated tooth can be viewed. The U-shaped nature of this anti-splash device prevents the aqueous fluid from being directed at all desired portions of an associated tooth, particularly posterior regions thereof, due to the existence of the depending leg opposite the nozzle. Thus, while a degree of anti-splash is certainly provided by this device, its usefulness is suspect.

Other patented dental devices of lesser interest include U.S. Pat. Nos. 2,720,702 in the name Hyman Freedman, 2,731,722 in the name of Jesse Wilen, 3,909,867 in the name Gunnar Hogsell and 4,850,868 in the name of Gerard Wright et al.

SUMMARY OF THE INVENTION

In keeping with the foregoing, the present invention is directed to a novel deflector shield particularly adapted for assembly upon a nozzle of a dental air/water/spray syringe which includes a one-piece homogeneous body of transparent polymeric/copolymeric synthetic plastic material having a central portion surrounded by a peripheral portion with the central portion including an opening and/or a tube with a bore for assembly upon a dental air/water/spray syringe nozzle. The peripheral portion includes a concave surface for deflecting material impinging thereagainst which is reflected from the interior of a patient's mouth. Since the deflector shield is transparent and essentially seals against the nozzle of the syringe, virtually all reflected material which contacts the concave surface of the deflector shield is redirected thereby along a flow path back toward the interior of a patient's mouth, thus precluding undesired and potentially harmful side effects to the operator/dentist/assistant.

Because the deflector shield is constructed from transparent material, it can be positioned immediately adjacent the tip of the syringe nozzle which places the concave surface immediately adjacent the operative zone in the patient's mouth which renders the reflected material flow path extremely short. Therefore, since the deflector shield can be placed proximate the area of air/water/spray impingement, the reflected material cannot widely diverge and thus most, if not all, will contact the concave surface of the deflector shield and will be redirected away from the operator/dentist/assistant. Thus, the operating zone can be clearly viewed by the operator/dentist/assistant, yet the latter are virtually assured that they will not be adversely affected by materials reflected from the patient's mouth.

With the above, and other objects in view that will hereinafter appear, the nature of the invention will be more clearly understood by reference to the following detailed descriptio, the appended claims and the several views illustrated in the accompanying drawing.

BRIEF DESCRIPTION OF THE DRAWING

FIG. 1 is a fragmentary perspective view of a dental syringe, and illustrates a deflector shield of the present invention carried by a nozzle of the syringe.

FIG. 2 is a perspective view of the deflector shield of the present invention, and illustrates a body thereof including a central tubular portion and a peripheral portion in outboard surrounding relationship thereto.

FIG. 3 is an enlarged cross sectional view taken generally along line 3—3 of FIG. 2, and illustrates details of the central and peripheral portions of the body which is also of a one-piece homogeneous synthetic polymeric/copolymeric transparent construction.

FIG. 4 is an end view of the nozzle and deflector shield of FIG. 1, and illustrates air and water ports of the nozzle and a concave surface of the deflector shield.

FIG. 5 is a fragmentary side elevational view of another deflector shield of this invention associated with another nozzle, and in this embodiment the deflector shield has a relatively long tubular central portion terminated adjacent a bent portion of the nozzle.

FIG. 6 is an axial enlarged cross sectional view of the deflector shield of FIG. 5, and illustrates details thereof including spaced parallel peripheral grooves along the tubular central portion for fracturing the tubular central portion to locate the deflector shield further from the terminal end of the nozzle than that illustrated in FIG. 5.

DESCRIPTION OF THE PREFERRED EMBODIMENTS

Reference is first made to FIG. 1 of the drawings in which is illustrated a dental syringe and deflector shield combination which is generally designated by the reference 10. The dental syringe and deflector shield combination 10 includes a dental syringe 11 having a hand piece 12 and a nozzle 13 defined by an elongated nozzle main portion 14, a bent portion 15 and a nozzle terminal end portion 16. The nozzle 13 includes a plurality of ports including a central port or passage 21 (FIG. 4) which is connected to a source of water and which is in turn controlled by a push button 22 upon the hand piece 12. Three other passages spaced 120° from each other define orifices 23 (FIG. 4) at an end face 17 of the nozzle terminal end portion 16 which are also in fluid communication with a pressurized source of air under the control of another push button 24 (FIG. 1) of the hand piece 12. If an operator/dentist/assistant depresses the button 22, water is emitted from the passage/port/orifice 21 (FIG. 4) into a zone of operation of a patient's mouth, as shown in FIG. 1 relative to a tooth T which may include a prepared or to-be-prepared cavity C. If the button 24 is depressed, but not the button 22, air is emitted from the passages, ports or orifices 23, again into the mouth of the patient in the area of the tooth T. If both buttons 22, 24 are depressed, both air and water (spray) are emitted into the area of the tooth T. The emitted spray, be it water alone, air alone, or a water/air spray is generally designated by the spray stream or flow path S in FIG. 1.

The dental syringe and deflector shield combination 10 also includes a deflector shield 30 illustrated in FIG. 1 assembled upon the nozzle terminal end portion 16.

The deflector shield 30 comprises a generally one-piece transparent homogeneous body of synthetic polymeric/copolymeric synthetic plastic material, such as transparent polycarbonate, crystal styrene, clear acrylic, silicone rubber or the like. The deflector shield or deflector shield body 30 is preferably injection molded and is preferably relatively rigid.

The deflector shield 30 includes a central portion 31 and a peripheral portion 32 generally surrounding the central portion 31.

The central portion 31 is generally a tubular portion having one end 34 projecting to one side (see FIG. 3) of the peripheral portion 32 and another end 35 projecting opposite thereto. Means 36 in the form of a bore or opening are provided through the tubular central portion 31 for slidably assembling the deflector shield 30 upon the nozzle terminal end portion 16, in the manner readily apparent from FIG. 1, namely, the diameter of the generally cylindrical opening or bore 36 is the same or slightly less than the exterior diameter of the nozzle terminal end portion 16 and a friction or force fit is achieved between the two. Means 38 in the form of a roughened or cross-grooved surface, as opposed to a smooth surface, may be provided to increase the frictional/gripping purchase between the assembling means 36 and the exterior surface (unnumbered) 17 of the nozzle terminal end portion 16.

The peripheral portion 32 includes opposite forward and rearward surface portions, namely, a concave forward surface portion 40 and a convex rearward surface portion 41. The concave surface 40 defines means for deflecting material impinging thereagainst during a dental procedure and redirecting the same along a flow path away from the operator/dentist/assistant. For example, in FIG. 1 the concave surface 40 is directed toward the cavity C of the tooth T into which the spray S is directed. Since the spray S is under pressure, the cavity C and/or the tooth T causes the spray S to be reflected in a direction outwardly of the patient's mouth and toward the operator/dentist/assistant, as indicated by reflected material flow paths R in FIG. 1. The reflected material may, of course, include not simply the air/water/spray in the injected stream S, but particles, saliva, blood, etc. admixed therewith and accumulated in the reflected flow paths R. Obviously, when the reflected flow paths R impinge/contact the concave surface 40 of the deflector shield 30, they will be redeflected away from the operator/dentist/assistant, as indicated by the redirected flow path D in FIG. 1. Hence, the reflected material R will not adversely affect the operator/dentist/assistant.

It is also to be noted that the deflector shield 30 is positioned extremely close (¼") to the end face 17 of the nozzle terminal end portion 16. Because the distance (¼") between the deflector shield 30 and the end face 17 of the nozzle terminal end portion 16 is quite small, the nozzle terminal end portion 16, when brought closely adjacent the cavity C and/or the tooth T, will obviously generate a relatively short length of the reflow material/spray R which additionally will reduce the tendency of the latter to diverge appreciably. Stated otherwise, the closer the deflector shield 30 can be placed adjacent the cavity C/tooth T, the less is the length of the reflow spray R and the less is its divergence assuring that virtually the entirety thereof will impinge against the concave surface 40 and be deflected thereby, as indicated by the deflected stream D. The latter operation is enhanced by the transparent nature of the deflector shield 30 as well as a radius R1 (FIG. 3) which generates the concave surface 40 from a locus L1 along an axis A1 of the tubular central portion 31 and the bore or opening 33 thereof. A like radius R2 from another locus L2 also located on the axis A1 generates the convex surface 41. The radii R1, R2 are identical (generally between 0.50–0.60 inch) but because they are generated at spaced loci L1, L2, the surfaces 40, 41 progressively taper in a direction toward a terminal edge 43 of the deflector shield 30. The latter construction allows the deflector shield 30 to be made of less material as compared to constructing the deflector shield 30 such as the surfaces 40, 41 would be parallel to each other.

Another deflector shield constructed in accordance with this invention is illustrated in FIGS. 5 and 6 of the drawings and is generally designated by the reference numeral 30'. The reference numerals in FIGS. 5 and 6 have been primed to indicate structure identical to that of the deflector shield 30. In the case of the deflector shield 30' it is to be noted that a tubular central portion 31' lacks an end corresponding to the end 35 of the deflector shield 30. Furthermore, an end 34' of the deflector shield 30' is longer than the end 34 of the deflector shield 30 and terminates in an annular end face 45. In addition, means in the form of a pair of axially spaced peripheral grooves 46 are formed in an exterior surface 47 of the end 34' to facilitate changing the overall axial length of the end 34'.

As shown in FIG. 5, the deflector shield 30' is assembled upon the nozzle terminal end portion 16' with its end face 45 generally at the juncture of the bent portion 15'. The deflector shield 30' cannot be moved further to the left and thus the abutment between the end face 45 and the bent portion 15' locates the deflector shield 30' and specifically the concave surface 40' thereof precisely the minimum distance (approximately ¼") desired from the terminal end face 17' of the nozzle terminal end portion 16'. Though most nozzles are standardized with respect to length, diameter, and the location of the various portions 14, 15 and 16 relative to each other, certain nozzles can vary in length and the location of the bent portion 15, and obviously an operator/dentist/assistant may wish to locate the concave surface 40' further from the terminal end face 17' of the nozzle terminal end portion 16'. In order to do so, all that need be done is to break the tubular end 34' along either one of the grooves 46 which will, of course, change the distance of the concave surface 40 from the terminal end face 17' of the nozzle terminal end portion 16' once the severed/fractured end of the end 34' is moved into the area of the bent portion 15'.

In lieu of the grooves 46, the overall deflector shield could be instead made from a less rigid material, such as transparent silicone rubber, in which case the tubular end 34' could be simply cut by a knife, razor, scalpel or surgical scissors.

Although a preferred embodiment of the invention has been specifically illustrated and described herein, it is to be understood that minor variations may be made in the apparatus without departing from the spirit and scope of the invention, as defined in the appended claims.

I claim:

1. A deflector shield particularly adapted for assembly upon a nozzle of a dental air/water syringe comprising a generally one-piece homogeneous body of transparent polymeric synthetic plastic material, said body including a central portion and a peripheral portion generally surrounding said central portion, said central portion including means for assembling said body upon a nozzle of a dental air/water syringe, said peripheral portion including concave surface means for deflecting undesirably reflected spray impinging thereagainst during a dental procedure along a redirected flow path away from the operator/dentist/assistant, said peripheral portion and said concave surface means being of sizes to permits placement of said deflector shield proximate the area of air/water impingement and adjacent an involved target area whereby reflected spray impinging against said concave surface means is limited in the length of its travel and minimized in its divergence thus insuring that virtually the entirety of the reflected spray impinges against the concave surface means and is redirected thereby, said peripheral portion including opposite forward and rearward surface portions, said concave surface means being defined by said forward surface portion, said central portion being of a tubular configuration, and said tubular central portion projecting beyond both of said forward and rearward surface portions.

2. A deflector shield particularly adapted for assembly upon a nozzle of a dental air/water syringe comprising a generally one-piece homogeneous body of transparent polymeric/copolymeric synthetic plastic material, said body including a central portion and a peripheral portion generally surrounding said central portion, said central portion including means for assembling said body upon a nozzle of a dental air/water syringe, said peripheral portion including concave surface means for deflecting undesirably reflected spray impinging thereagainst during a dental procedure along a redirected flow path away from the operator/dentist/assistant, said peripheral portion and said concave surface means being of sizes to permit placement of said deflector shield proximate the area of air/water impingement and adjacent an involved target area whereby reflected spray impinging against said concave surface means is limited in the length of its travel and minimized in its divergence thus insuring that virtually the entirety of the reflected spray impinges against the concave surface means and is redirected thereby, said central portion being of a tubular configuration, said assembling means being an opening of said tubular central portion, said tubular central portion being of a predetermined axial length, means for reducing the axial length of said tubular central portion, and said axial length reducing means including weakening means along which said tubular central portion is adapted to be fractured at a desired length.

3. A dental syringe and deflector shield combination comprising a dental syringe having a nozzle including a forward terminal end portion through which at least one of air and water can be directed by an operator into a patient's mouth with attendant undesired reflection of material from the patient's mouth; a deflector shield comprising a generally one-piece homogeneous body of transparent polymeric/copolymeric synthetic plastic material, said body including a central portion and a peripheral portion generally surrounding said central portion, said central portion including means for assembling said body upon said forward terminal end portion, said peripheral portion including concave surface mean for deflecting undesirably reflected spray along a redirected flow path back toward the interior of a patient's mouth, said peripheral portion and said concave surface means being of sizes to permit placement of said deflector shield proximate the area of air/water impingement and adjacent an involved target area whereby reflected spray impinging against said concave surface means is limited in the length of its travel and minimized in its divergence thus insuring that virtually the entirety of the reflected spray impinges against the concave surface means and is redirected thereby, said peripheral portion including opposite forward and rearward surface portions, said concave surface means being defined by said forward surface portion, said central portion being of a tubular configuration, and said tubular central portion projecting beyond both of said forward and rearward surface portions.

4. A dental syringe and deflector shield combination comprising a dental syringe having a nozzle including a forward terminal end portion through which at least one of air and water can be directed by an operator into a patient's mouth with attendant undesired reflection of material from the patient's mouth; a deflector shield comprising a generally one-piece homogeneous body of transparent polymeric/copolymeric synthetic plastic material, said body including a central portion and a peripheral portion generally surrounding said central portion, said central portion including means for assembling said body upon said forward terminal end portion, said peripheral portion including concave surface means for deflecting undesirably reflected spray along a redirected flow path back toward the interior of a patient's mouth, said peripheral portion and said concave surface means being of sizes to permit placement of said deflector shield proximate the area of air/water impingement and adjacent an involved target area whereby reflected spray impinging against said concave surface means is limited in the length of its travel and minimized in its divergence thus insuring that virtually the entirety of the reflected spray impinges against the concave surface means and is redirected thereby, said central portion being of a tubular configuration, said tubular central portion being of a predetermined axial length, means for reducing the axial length of said tubular central portion, and said axial length reducing means including weakening means along which said tubular central portion is adapted to be fractured.

* * * * *